US007243406B1

(12) United States Patent
Wray

(10) Patent No.: US 7,243,406 B1
(45) Date of Patent: Jul. 17, 2007

(54) CASKET WITH COMBINATION HINGE, BRACE, AND LOCK

(75) Inventor: Gregory W. Wray, Guilford, IN (US)

(73) Assignee: Batesville Services, Inc., Batesville, IN (US)

( * ) Notice: Subject to any disclaimer, the term of this patent is extended or adjusted under 35 U.S.C. 154(b) by 0 days.

(21) Appl. No.: 11/371,528

(22) Filed: Mar. 9, 2006

(51) Int. Cl.
*A61F 17/00* (2006.01)

(52) U.S. Cl. .................. 27/18; 27/17; 16/326; 16/328; 16/353

(58) Field of Classification Search .................... 27/18, 27/17, 16, 14, 2, DIG. 1; 16/321, 326, 327, 16/328, 349, 352, 353
See application file for complete search history.

(56) References Cited

U.S. PATENT DOCUMENTS

| | | | | | |
|---|---|---|---|---|---|
| 170,702 | A | | 12/1875 | Becket, Jr. | |
| 543,533 | A | | 7/1895 | Krupp | |
| 706,398 | A | | 8/1902 | Emst | |
| 1,151,397 | A | | 9/1915 | Robinson | |
| 1,533,401 | A | | 4/1925 | Gale | |
| 1,868,342 | A | | 7/1932 | Yurkovitch | |
| 2,156,872 | A | * | 5/1939 | Roberts | 24/329 |
| 2,431,263 | A | | 11/1947 | Lundgren | 4/236 |
| 2,578,153 | A | | 12/1951 | Schmitz | 4/236 |
| 2,848,783 | A | * | 8/1958 | Keller, Jr. et al. | 27/18 |
| 2,971,803 | A | * | 2/1961 | Frederick | 16/326 |
| 3,060,546 | A | * | 10/1962 | Nelson | 27/18 |
| 3,811,150 | A | | 5/1974 | Chalmers | 16/137 |
| 3,959,859 | A | | 6/1976 | Stein, Jr. et al. | 27/18 |
| 4,340,992 | A | | 7/1982 | Lombardi | 16/349 |
| 4,360,953 | A | * | 11/1982 | Angermann | 27/14 |
| 4,524,496 | A | | 6/1985 | Tehsildar et al. | 27/18 |
| 4,925,223 | A | * | 5/1990 | Craft | 292/339 |
| 5,060,993 | A | | 10/1991 | Maier | 292/241 |
| 5,503,439 | A | | 4/1996 | LaJeunesse et al. | 292/44 |
| 5,570,493 | A | | 11/1996 | Gulick | 27/18 |
| 5,765,268 | A | * | 6/1998 | MacKirdy | 27/18 |
| 5,966,786 | A | | 10/1999 | Bowling | 27/2 |
| 6,154,938 | A | | 12/2000 | LaJeunesse et al. | 27/2 |

* cited by examiner

*Primary Examiner*—William L. Miller
(74) *Attorney, Agent, or Firm*—Wood, Herron & Evans LLP

(57) ABSTRACT

A casket comprises a casket shell having a pair of side walls, a pair of end walls, and a bottom wall, a casket lid pivoted to the casket shell for movement to an open position and to a closed position, and a combination hinge, brace, and lock mechanism connecting the lid to the shell. The mechanism comprises a first hinge plate secured to the shell, a second hinge plate secured to the lid, the first and second hinge plates pivoted to one another, and a latch bar moveably mounted relative to the first and second hinge plates for movement to first, second, and third positions. The latch bar and hinge plates are configured such that when the latch bar is in the first position the latch bar fixes the hinge plates relative to one another such that the lid is fixed in the closed position. When the latch bar is in the second position the hinge plates are free to pivot relative to one another such that the lid is free to pivot relative to the shell. When the latch bar is in the third position the latch bar fixes the hinge plates relative to one another such that the lid is fixed in the open position.

8 Claims, 4 Drawing Sheets

CASKET WITH COMBINATION HINGE, BRACE, AND LOCK

FIELD

Figure 1:
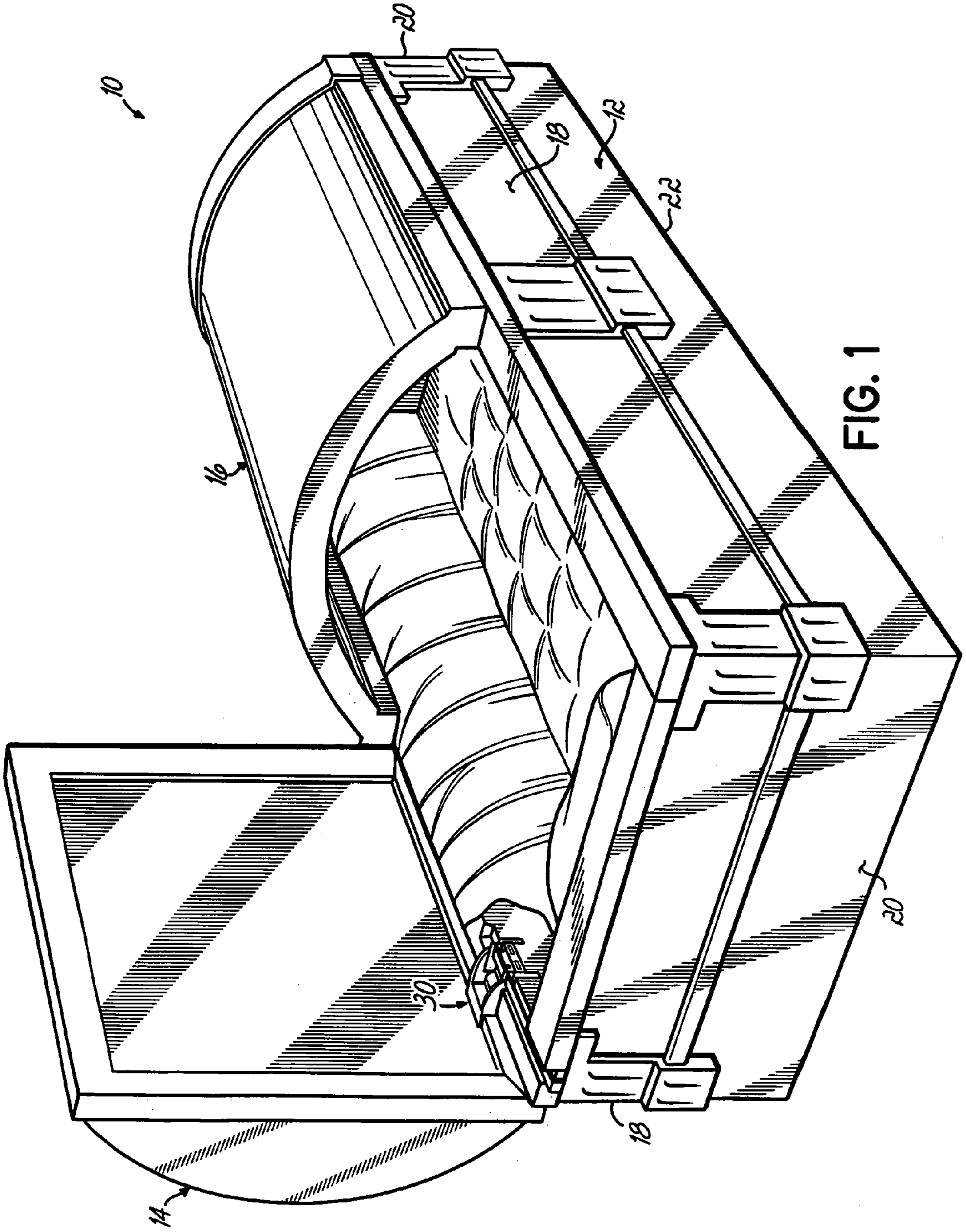

This invention relates generally to funerary products, and more particularly to caskets and casket hinges, braces, and locks.

BACKGROUND

A casket has a shell and a lid or pair of lids pivoted to the shell by a hinge. Caskets also typically include a "brace," a mechanism to retain the lid in the open position and to prevent the lid inadvertently closing. Examples of casket brace mechanisms are shown in the assignee's U.S. Pat. Nos. 3,959,859 and 5,570,493, hereby incorporated by reference herein. Caskets also typically include a locking mechanism to lock the lid in the closed position. Examples of casket lock mechanisms are shown in the assignee's U.S. Pat. Nos. 5,060,993, 5,503,439, 5,966,786 and 6,154,938, hereby incorporated by reference herein.

A casket which includes a lid hinge, a lid brace, and a lid lock thus may have as many as three separate mechanisms for accomplishing the hinging, bracing, and locking functions. The number of such separate mechanisms, and the combined total number of parts of the mechanisms, increases the cost of manufacturing the casket.

SUMMARY

In one aspect, a casket comprises a casket shell having a pair of side walls, a pair of end walls, and a bottom wall, a casket lid pivoted to the casket shell for movement to an open position and to a closed position, and a combination hinge, brace, and lock mechanism connecting the lid to the shell. The mechanism comprises a first hinge plate secured to the shell, a second hinge plate secured to the lid, the first and second hinge plates pivoted to one another, and a latch bar moveably mounted relative to the first and second hinge plates for movement to first, second, and third positions. The latch bar and hinge plates are configured such that when the latch bar is in the first position the latch bar fixes the hinge plates relative to one another such that the lid is locked in the closed position. When the latch bar is in the second position the hinge plates are free to pivot relative to one another such that the lid is free to pivot relative to the shell. When the latch bar is in the third position the latch bar fixes the hinge plates relative to one another such that the lid is retained in the open position.

In another aspect, a casket comprises a casket shell having a pair of side walls, a pair of end walls, and a bottom wall, a casket lid pivoted to the casket shell for movement to an open position and to a closed position, and a combination hinge and brace mechanism connecting the lid to the shell. The mechanism comprises a first hinge plate secured to the shell, a second hinge plate secured to the lid, the first and second hinge plates pivoted to one another, and a latch bar moveably mounted relative to the first and second hinge plates for movement to first and second positions. The latch bar and hinge plates are configured such that when the latch bar is in the first position the hinge plates are free to pivot relative to one another such that the lid is free to pivot relative to the shell. When the latch bar is in the second position the latch bar fixes the hinge plates relative to one another such that the lid is retained in the open position.

In yet another aspect, a casket comprises a casket shell having a pair of side walls, a pair of end walls, and a bottom wall, a casket lid pivoted to the casket shell for movement to an open position and to a closed position, and a combination hinge and lock mechanism connecting the lid to the shell. The mechanism comprises a first hinge plate secured to the shell, a second hinge plate secured to the lid, the first and second hinge plates pivoted to one another, and a latch bar moveably mounted relative to the first and second hinge plates for movement to first and second positions. The latch bar and hinge plates are configured such that when the latch bar is in the first position the hinge plates are free to pivot relative to one another such that the lid is free to pivot relative to the shell. When the latch bar is in the second position the latch bar fixes the hinge plates relative to one another such that the lid is locked in the closed position.

In still another aspect, a casket comprises a casket shell having a pair of side walls, a pair of end walls, and a bottom wall, a casket lid pivoted to the casket shell for movement to an open position and to a closed position, and a combination brace and lock mechanism connecting the lid to the shell. The mechanism comprises a first plate secured to the shell, a second plate secured to the lid, and a latch bar moveably mounted relative to the first and second hinge plates for movement to first and second positions. The latch bar and hinge plates are configured such that when the latch bar is in the first position the latch bar fixes the hinge plates relative to one another such that the lid is retained in the open position. When the latch bar is in the second position the latch bar fixes the hinge plates relative to one another such that the lid is locked in the closed position.

In a further aspect, a combination hinge, brace, and lock mechanism adapted to connect a casket lid to a casket shell, the lid pivoted to the shell for movement to an open position and a closed position, comprises a first hinge plate adapted to be secured to the shell, a second hinge plate adapted to be secured to the lid, the first and second hinge plates pivoted to one another, and a latch bar moveably mounted relative to the first and second hinge plates for movement to first, second, and third positions. The latch bar and hinge plates are configured such that when the latch bar is in the first position the latch bar fixes the hinge plates relative to one another such that the lid is locked in the closed position. When the latch bat is in the second position the hinge plates are free to pivot relative to one another such that the lid is free to pivot relative to the shell. When the latch bar is in the third position the latch bar fixes the hinge plates relative to one another such that the lid is retained in the open position.

The first hinge plate can comprise a base plate and a pair of opposed side plates. Each of the side plates can include a slot for accommodating the latch bar. The second hinge plate can comprise a base plate and a pair of opposed side plates. The side plates of the hinge plates can be pivoted together. The side plates of the second hinge plate can include a pair of spaced apart notches therein. The latch bar can include a pair of spaced apart notches therein. The hinge plates and latch bar can cooperate in such a manner that when the side plates of the second hinge plate are positioned in the notches of the latch bar, the hinge plates are free to pivot relative to one another, and when the latch bar is positioned in either of the pair of notches in the side walls of the second hinge plate the hinge plates are fixed relative to one another. A spring, operable between the first hinge plate and the latch bar, can be included to urge the latch bar to an outward position relative to the first hinge plate.

DRAWINGS

Figure 2:
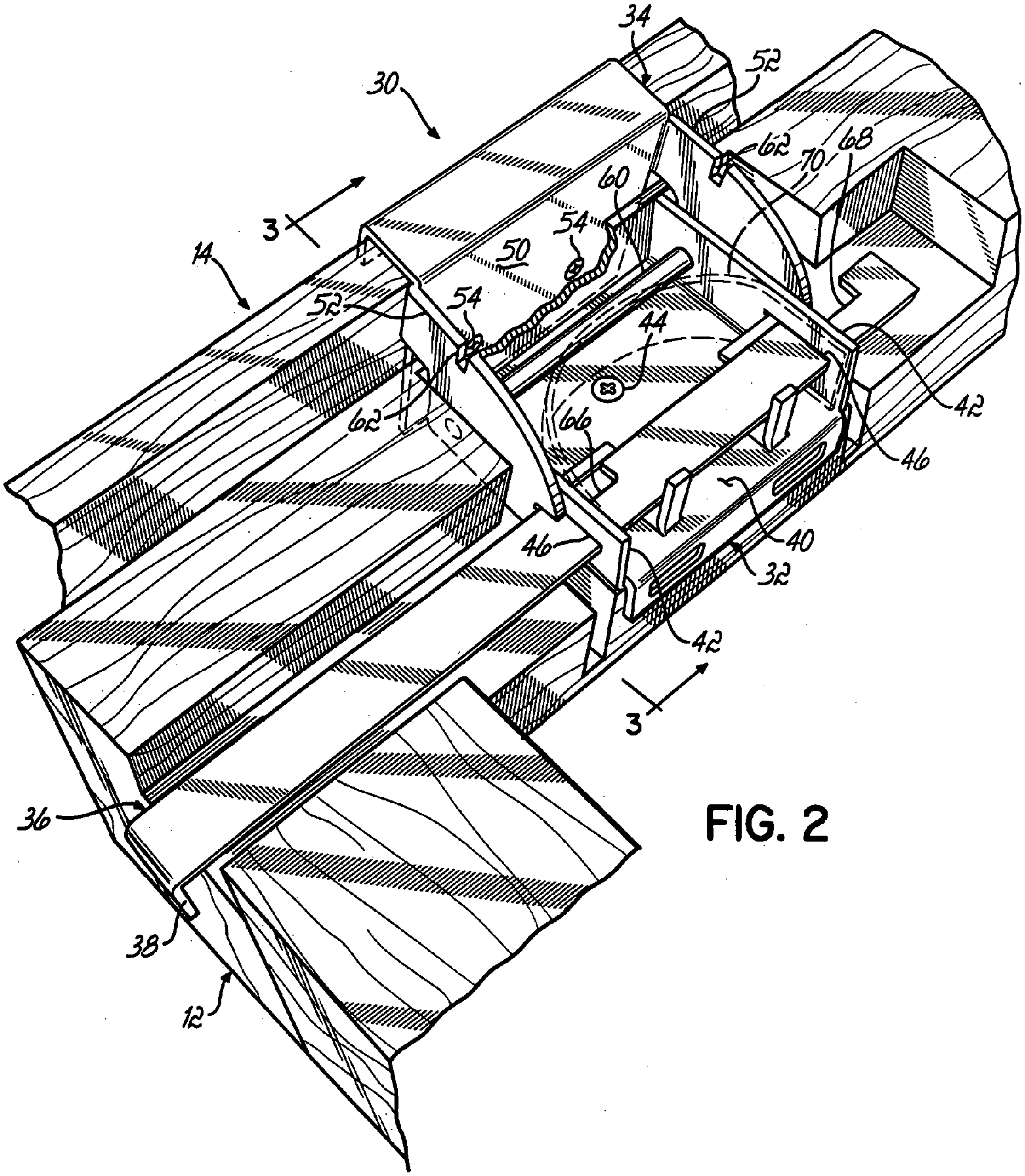
Figure 3:
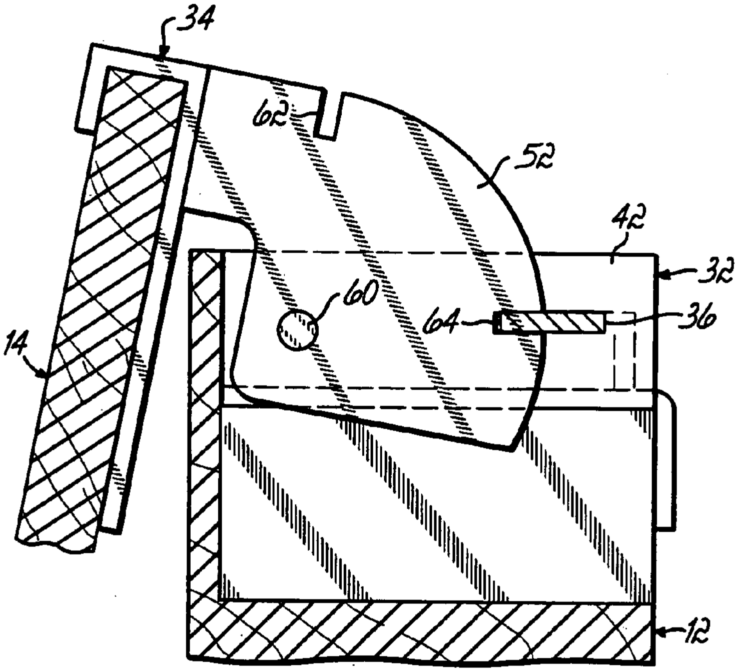
Figure 4:
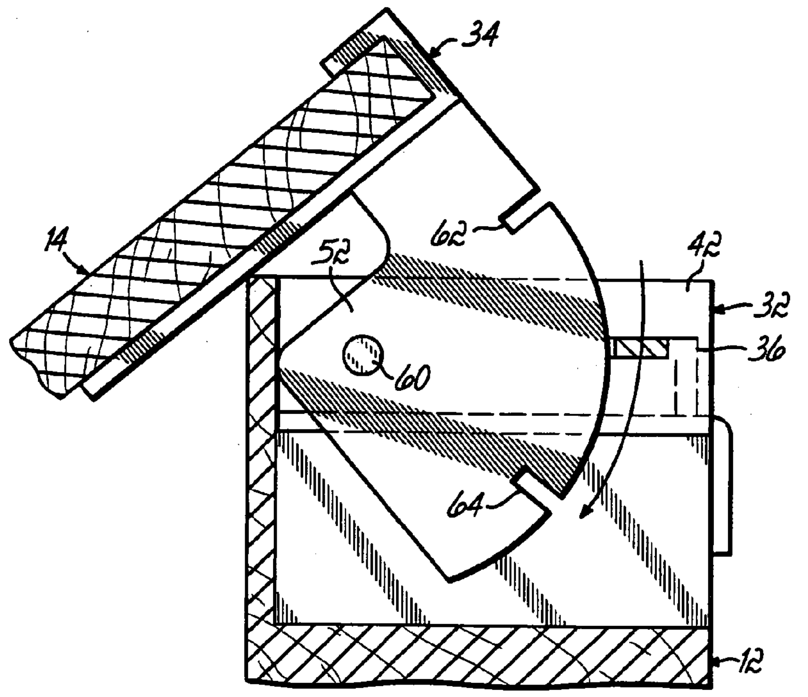
Figure 5:
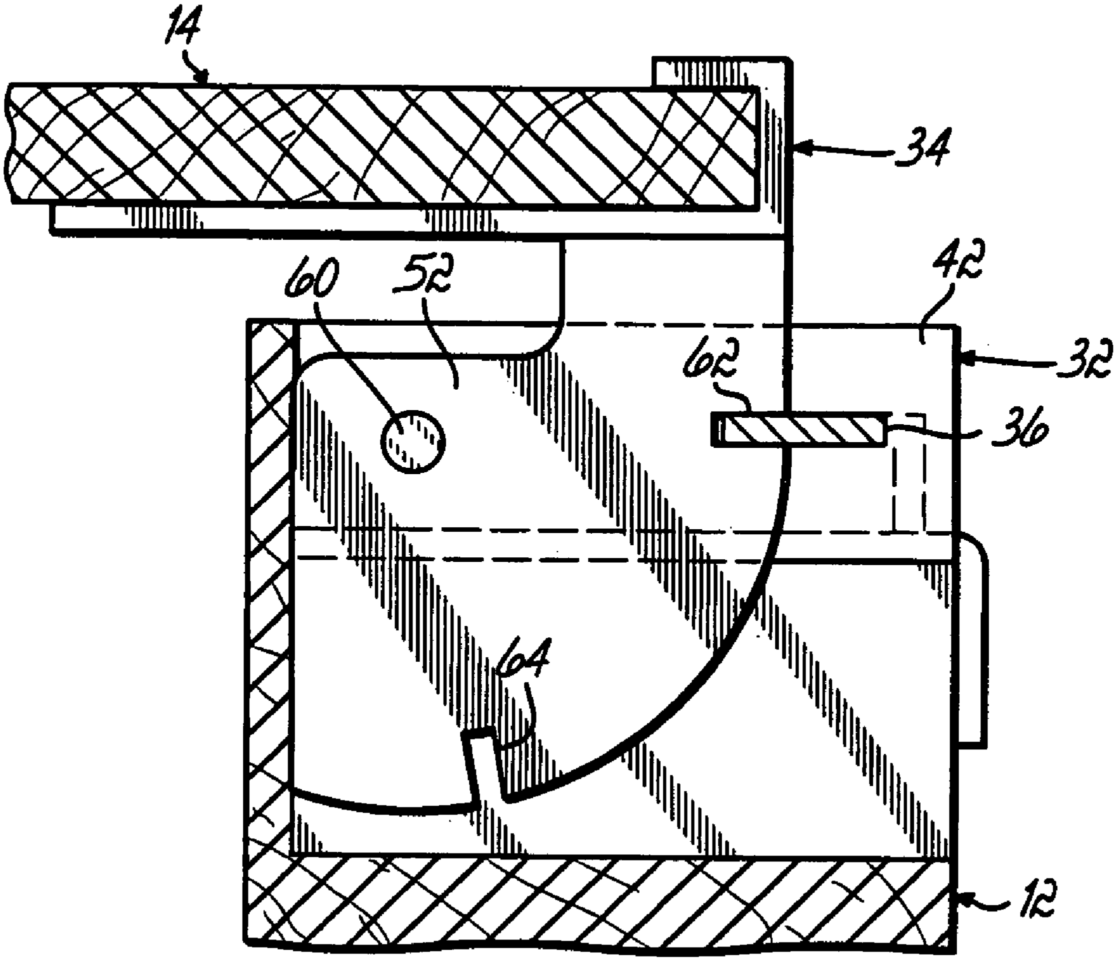

FIG. 1 is a perspective view of a casket and combination hinge, brace, and lock, FIG. 2 is an enlarged perspective view of the combination hinge, brace, and lock of FIG. 1, FIG. 3 is a side view of the combination hinge, brace, and lock of FIGS. 1 and 2 with the lid of the casket retained in the open position (bracing function), FIG. 4 is a view similar to FIG. 3 but with the lid of the casket shown being moved from the open position to the closed position (hinging function), and FIG. 5 is a view similar to FIGS. 3 and 4 but with the lid of the casket locked in the closed position (locking function).

DESCRIPTION

Referring first to FIG. 1, there is illustrated a casket 10 comprising a shell 12 and a lid 14 (or pair of lids 14, 16) closeable on the shell 12. Shell 12 has a pair of side walls 18, 18, and pair of end walls 20, 20, and a bottom wall 22. A combination hinge, brace, and lock mechanism 30 connects the lid 14 to the shell 12.

Referring now to FIGS. 2–4, mechanism 30 comprises a first hinge plate 32, a second hinge plate 34 pivoted to first hinge plate 32, and a latch bar 36. The latch bar 36 is moveably mounted relative to the first and second hinge plates 32, 34 for movement to first, second, and third positions. As will be described below in more detail, the latch bar 36 and hinge plates 32, 34 are configured such that when the latch bar 36 is in the first position the latch bar 36 fixes the hinge plates relative to one another such that the lid is locked in the closed position (locking function, FIG. 5). When the latch bar 36 is in the second position the hinge plates 32, 34 are free to pivot relative to one another such that the lid 14 is free to pivot relative to the shell 12 (hinging function, FIG. 4). When the latch bar 36 is in the third position the latch bar 36 fixes the hinge plates 32, 34 relative to one another such that the lid 14 is retained in the open position (bracing function, FIG. 3). Latch bar 36 can have a downturned end 38 to facilitate manipulation thereof.

First hinge plate 32 can comprise a base plate 40 and a pair of opposed side plates 42, 42. Base plate 40 can be secured to lid 14 with fasteners, for example screws 44. Each of the side plates 42 can include a slot 46 for accommodating the latch bar 36. The second hinge plate 34 can comprise a base plate 50 and a pair of opposed side plates 52, 52. Base plate 50 can be secured to lid 14 with fasteners, for example screws 54. The side plates 52, 52 of the second hinge plate 34 can be pivoted to the side plates 42, 42 of the first hinge plate 32 by, for example, a pin 60 having ends fixed to side plates 52, 52 and passing through pivot holes in side plates 42, 42. The side plates 52, 52 of second hinge plate 34 can each have a pair of spaced apart notches 62, 64 formed therein. The latch bar 36 can similarly have a pair of spaced apart notches 66, 68 formed therein.

The hinge plates 52, 52 and the latch bar 36 can thus cooperate in the following manner. When the side plates 52, 52 of the second hinge plate 34 are positioned in the notches 66, 68 of the latch bar 36, the hinge plates 32, 34 are free to pivot relative to one another. Lid 14 can thus be raised or lowered when the side plates 52, 52 and latch bar 36 are in this position. See FIG. 4. When the end 38 of the latch bar 36 is manipulated such that the latch bar 36 is positioned in either of the pair of notches 62, 64, hinge plates 32, 34 are not free to pivot relative to each other. When latch bar 36 is in slots 64 in side plates 52, 52, the lid 14 is retained in the open position. See FIG. 3. When latch bar 36 is in slots 62 in side plates 52, 52, the lid 14 is locked in the closed position. See FIG. 5.

A spring, for example leaf spring 70, can be incorporated into mechanism 30. Operable between first hinge plate 32 and latch bar 36, spring 70 biases latch bar 36 in such a manner as to urge latch bar 36 outwardly relative to first hinge plate 32 and shell 12.

The embodiments of the invention shown and described are for illustrative purposes only. The drawings and the description shall not limit in any way the scope of the invention as defined in the claims. While those skilled in the art may make various changes to, or additional embodiments of, the invention, none of those changes/embodiments will depart from the spirit of the invention. Thus, all such changes/embodiments shall be embraced by the scope of the invention as defined in the claims.

For example, while it may be preferred to include structure for performing all three of the hinging, bracing, and locking functions all in a single mechanism, other combinations and permutations are entirely within the scope of the invention. For example, the single mechanism could include only structure to perform just the hinging and bracing functions, or only structure to perform just the hinging and locking functions, or only structure to perform just the bracing and locking functions. All such combinations and permutations shall be embraced by the scope of the invention.

Accordingly, the invention is to be limited only by the scope of the following claims and their equivalents.

What is claimed is:

1. A casket comprising:

a casket shell having a pair of side walls, a pair of end walls, and a bottom wall, a casket lid pivoted to said casket shell for movement to an open position and to a closed position, and a combination hinge, brace, and lock mechanism connecting said lid to said shell, said mechanism comprising:

a first hinge plate secured to said shell, a second hinge plate secured to said lid, said first and second hinge plates pivoted to one another, and a latch bar moveably mounted to at least one of said first and second hinge plates for movement to first, second, and third positions, said latch bar and hinge plates configured such that when said latch bar is in said first position said latch bar fixes said hinge plates relative to one another such that said lid is fixed in the closed position, when said latch bar is in said second position said hinge plates are free to pivot relative to one another such that said lid is free to pivot relative to said shell, and when said latch bar is in said third position said latch bar fixes said hinge plates relative to one another such that said lid is fixed in the open position.

2. A casket comprising:

a casket shell having a pair of side walls, a pair of end walls, and a bottom wall, a casket lid pivoted to said casket shell for movement to an open position and to a closed position, and a combination hinge and brace mechanism connecting said lid to said shell, said mechanism comprising:

a first hinge plate secured to said shell, a second hinge plate secured to said lid, said first and second hinge plates pivoted to one another, and a latch bar moveably mounted to at least one of said first and second hinge plates for movement to first and second positions, said latch bar and hinge plates configured such that when said latch bar is in said first position said hinge plates are free to pivot relative to one another such that said lid is free to pivot relative to said shell, and when said latch bar is in said second position said latch bar fixes said hinge plates relative to one another such that said lid is fixed in the open position.

3. A casket comprising:

a casket shell having a pair of side walls, a pair of end walls, and a bottom wall, a casket lid pivoted to said casket shell for movement to an open position and to a closed position, and a combination hinge and lock mechanism connecting said lid to said shell, said mechanism comprising:

a first hinge plate secured to said shell, a second hinge plate secured to said lid, said first and second hinge plates pivoted to one another, and a latch bar moveably mounted to at least one of said first and second hinge plates for movement to first and second positions, said latch bar and hinge plates configured such that when said latch bar is in said first position said hinge plates are free to pivot relative to one another such that said lid is free to pivot relative to said shell, and when said latch bar is in said second position said latch bar fixes said hinge plates relative to one another such that said lid is fixed in the closed position.

4. A casket comprising:

a casket shell having a pair of side walls, a pair of end walls, and a bottom wall, a casket lid pivoted to said casket shell for movement to an open position and to a closed position, and a combination brace and lock mechanism connecting said lid to said shell, said mechanism comprising:

a first hinge plate secured to said shell, a second hinge plate secured to said lid, said first and second hinge plates pivoted to one another, and a latch bar moveably mounted to at least one of said first and second hinge plates for movement to first and second positions, said latch bar and hinge plates configured such that when said latch bar is in said first position said latch bar fixes said hinge plates relative to one another such that said lid is fixed in the open position, and when said latch bar is in said second position said latch bar fixes said hinge plates relative to one another such that said lid is fixed in the closed position.

5. The casket of any of claims 1–4 wherein:

said first hinge plate comprises a base plate and a pair of opposed side plates, each of said side plates including a slot for accommodating said latch bar, said second hinge plate comprises a base plate and a pair of opposed side plates, said side plates of said second hinge plate are pivoted to said side plates of said first hinge plate, each of said side plates of said second hinge plate includes a pair of spaced apart notches therein, said latch bar includes a pair of spaced apart notches therein, said hinge plates and said latch bar cooperate in such a manner that when said side plates of said second hinge plate are positioned in said notches of said latch bar, said hinge plates are free to pivot relative to one another, and when said latch bar is positioned in either of said pair of notches in said side walls of said second hinge plate said hinge plates are fixed relative to one another.

6. The casket of claim 5 further including a spring operable between said first hinge plate and said latch bar urging said latch bar to an outward position relative to said first hinge plate.

7. A combination hinge, brace, and lock mechanism adapted to connect a casket lid to a casket shell, the lid pivoted to the shell for movement to an open position and a closed position, said mechanism comprising:

a first hinge plate adapted to be secured to the shell, a second hinge plate adapted to be secured to the lid, said first and second hinge plates pivoted to one another, and a latch bar moveably mounted relative to said first and second hinge plates for movement to first, second, and third positions, said latch bar and hinge plates configured such that when said latch bar is in said first position said latch bar fixes said hinge plates relative to one another such that said lid is fixed in the closed position, when said latch bar is in said second position said hinge plates are free to pivot relative to one another such that said lid is free to pivot relative to said shell, and when said latch bar is in said third position said latch bar fixes said hinge plates relative to one another such that said lid is fixed in the open position said first hinge plate comprises a base plate and a pair of opposed side plates, each of said side plates including a slot for accommodating said latch bar, said second hinge plate comprises a base plate and a pair of opposed side plates, said side plates of said second hinge plate are pivoted to said side plates of said first hinge plate, each of said side plates of said second hinge plate includes a pair of spaced apart notches therein, said latch bar includes a pair of spaced apart notches therein, and said hinge plates and said latch bar cooperate in such a manner that when said side plates of said second hinge plate are positioned in said notches of said latch bar, said hinge plates are free to pivot relative to one another, and when said latch bar is positioned in either of said pair of notches in said side walls of said second hinge plate said hinge plates are fixed relative to one another.

8. The combination of claim 7 further including a spring operable between said first hinge plate and said latch bar urging said latch bar to an outward position relative to said first hinge plate.

* * * * *